(12) United States Patent
Fusco

(10) Patent No.: US 8,951,582 B2
(45) Date of Patent: *Feb. 10, 2015

(54) COMPOSITIONS FOR TOPICAL TREATMENT

(71) Applicant: Normajean Fusco, Unionville, NY (US)

(72) Inventor: Normajean Fusco, Unionville, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/070,486

(22) Filed: Nov. 2, 2013

(65) Prior Publication Data

US 2014/0343158 A1   Nov. 20, 2014

Related U.S. Application Data

(62) Division of application No. 13/895,354, filed on May 15, 2013, now Pat. No. 8,603,550.

(51) Int. Cl.

| | | |
|---|---|---|
| *A01N 65/00* | (2009.01) | |
| *A61K 31/14* | (2006.01) | |
| *A01N 33/12* | (2006.01) | |
| *A01N 37/36* | (2006.01) | |
| *A61K 8/34* | (2006.01) | |
| *A61K 8/36* | (2006.01) | |
| *A61K 8/37* | (2006.01) | |
| *A61K 8/41* | (2006.01) | |
| *A61K 8/43* | (2006.01) | |
| *A61K 8/46* | (2006.01) | |
| *A61Q 17/00* | (2006.01) | |
| *A61K 8/84* | (2006.01) | |
| *A61K 8/891* | (2006.01) | |
| *A61K 8/97* | (2006.01) | |
| *A61K 31/045* | (2006.01) | |
| *A61K 31/155* | (2006.01) | |
| *A61K 31/22* | (2006.01) | |
| *A61K 36/185* | (2006.01) | |
| *A61K 36/28* | (2006.01) | |

(52) U.S. Cl.
CPC .............. *A61K 31/14* (2013.01); *A01N 33/12* (2013.01); *A01N 37/36* (2013.01); *A61K 8/34* (2013.01); *A61K 8/342* (2013.01); *A61K 8/361* (2013.01); *A61K 8/37* (2013.01); *A61K 8/416* (2013.01); *A61K 8/43* (2013.01); *A61K 8/463* (2013.01); *A61Q 17/005* (2013.01); *A61K 8/84* (2013.01); *A61K 8/891* (2013.01); *A61K 8/97* (2013.01); *A61K 31/045* (2013.01); *A61K 31/155* (2013.01); *A61K 31/22* (2013.01); *A61K 36/185* (2013.01); *A61K 36/28* (2013.01)
USPC ........................................................ 424/725

(58) Field of Classification Search
None
See application file for complete search history.

(56) References Cited

U.S. PATENT DOCUMENTS

| | | |
|---|---|---|
| 5,879,684 A | 3/1999 | Fox et al. |
| 5,997,893 A | 12/1999 | Jampani et al. |
| 6,022,551 A | 2/2000 | Jampani et al. |
| 6,022,565 A | 2/2000 | Albert et al. |
| 6,528,070 B1 | 3/2003 | Bratescu et al. |
| 7,078,050 B2 | 7/2006 | Fusco |
| 7,842,726 B2 | 11/2010 | Aoki et al. |
| 7,871,649 B2 | 1/2011 | Modak et al. |
| 8,173,143 B2 | 5/2012 | Tecco et al. |
| 8,198,326 B2 | 6/2012 | Scholz |
| 8,293,802 B2 | 10/2012 | Modak et al. |
| 8,337,872 B2 | 12/2012 | Fuls et al. |
| 2002/0034524 A1 | 3/2002 | Poret |
| 2003/0049212 A1 | 3/2003 | Robinson et al. |
| 2004/0022822 A1 | 2/2004 | Poret |
| 2004/0161435 A1 | 8/2004 | Gupta |
| 2005/0025737 A1 | 2/2005 | Sebagh |
| 2005/0053595 A1 | 3/2005 | Fusco |
| 2005/0084471 A1 | 4/2005 | Andrews et al. |
| 2005/0249763 A1 | 11/2005 | Legendre et al. |
| 2006/0115440 A1 | 6/2006 | Arata et al. |
| 2009/0186943 A1 | 7/2009 | Ikeda et al. |
| 2009/0197948 A1 | 8/2009 | Miyahara et al. |
| 2009/0203649 A1 | 8/2009 | Kato et al. |
| 2009/0214628 A1 | 8/2009 | de Rijk |
| 2009/0226498 A1 | 9/2009 | Flugge-Berendes et al. |
| 2010/0196504 A1 | 8/2010 | Schmaus et al. |
| 2010/0216889 A1 | 8/2010 | Modak et al. |
| 2011/0070316 A1 | 3/2011 | Modak et al. |
| 2012/0148516 A1 | 6/2012 | Abel et al. |

(Continued)

OTHER PUBLICATIONS

Lonzagard Benzethonium Chloride USP, Revised Feb. 24, 2009. Lonza, Inc.
Bisabolol, Wikipedia, last modified Oct. 9, 2012.

(Continued)

*Primary Examiner* — Michael Meller
(74) *Attorney, Agent, or Firm* — Michael E. Zall

(57) ABSTRACT

A stable, self-preserving, antimicrobial, composition suitable for the treatment of a variety of dermal as well as subcutaneous conditions. The compositions include as an active ingredient a quaternary ammonium compound, preferably benzethonium chloride, potentiated and synergized with menthyl lactate cooling agent in a cationic carrier. Optionally, a phenoxyethanol preservative and chlorhexidine digluconate antibacterial agent may be used to assist in enhancing the activity. The compositions kill a broad spectrum of gram-negative and gram-positive bacteria, fungus and yeasts. The compositions are used as first aid skin treatments and as skin sanitizers to help prevent bacterial contamination of minor cuts, scrapes and burns. The compositions are particularly useful when applied to the skin after hair removal in that they additionally cool, soothe and moisturize the skin. The compositions may also serve as a base vehicle in which additional skin care ingredients may be added to provide additional functionality to the compositions.

6 Claims, No Drawings

(56) References Cited

U.S. PATENT DOCUMENTS

2012/0201902 A1 8/2012 Modak et al.
2012/0276219 A1 11/2012 Taylor et al.

OTHER PUBLICATIONS

Chamomile, from Wikipedia, last modified Jan. 25, 2013.
Quat Chem, Chlorhexidine Digluconate (CHG20), Jan. 26, 2013 downloaded.
SharonBole Chemical Marketing, Frescolate ML (Liquid), Menthyl lactate, Jan. 26, 2013 downloaded.
Neolone PH 100 Preservative, Dow Microbial Control Product Information, Jan. 1, 2010.
Witch hazel (astringent), from Wikipedia, last modified on Jan. 1, 2013.
Benzelthonium chloride, from Wikipedia, last modified Sep. 22, 2012.
Cetyl alcohol, from Wikipedia, last modified Oct. 22, 2012.
Silicone Fluids—Clearco Products, Dimethicones, http://www.clearcoproducts com/ dimethicones.html, downloaded Jan. 26, 2013.
Dimethicone Cosmetic Ingredient (INCI), Last Update Aug. 23, 2010, http://www. specialchem 4cosmetics.com/.
Emery Oleochemicals LLC, MSD Emersol 132 NF Lilly Stearic Acid; May 29, 2009.
Cosmetic Ingredient: Effect of Eutanol G: Care Chemicals: Cognis; Apr. 7, 2003.
http://cosmetic-ingredient.blogspot.com/2012/01 /effect-of-eutanol-g.html, downloaded.
Eutanol G by BASF Care Creations, (C) 2012 Innovadex LLC.
Croda Personal Care—Incroquat Behenyl TMS-50; (C) 2013 Croda International Plc.
Cognis Corporation, Ultragel 300 MSD: Sep. 27, 2007.
Cosmetic Science Technology News; http://www.cosmeticsciencetechnology.com/profile.php?id=15, downloaded on Jan. 26, 2013.

COMPOSITIONS FOR TOPICAL TREATMENT

RELATED APPLICATION

This application is a divisional application of pending U.S. Ser. No. 13/895,354 filed on May 15, 2013 entitled *Compositions for Topical Treatment*, now U.S. Pat. No. 8,603,550, the entire disclosure of which is incorporated herein by reference.

BACKGROUND OF THE INVENTION

This invention relates generally to compositions for applying to the skin, and more particularly to an improved multi-purpose topically applied, self-preserving, antimicrobial, composition suitable for the treatment of a variety of dermal as well as subcutaneous conditions. The compositions may optionally be combined with other medicaments, wherein it serves as a vehicle for topical application. The compositions possess broad-spectrum rapid kill properties and are useful as skin sanitizers. The compositions are particularly useful for preventing microbial contamination of the skin after hair removal.

While many dermal conditions are the result of internal body chemistry, and require the services of a medical provider, many relatively simple skin conditions may often be treated at by using non-prescription (OTC) type remedies. Typical of such conditions are teenage acne, itching, swelling, as well as rashes caused by bacterial and microbial conditions. Individual remedies are known in the art for treating such conditions.

Some common pathogens that often cause skin infections include *Staphylococcus aureus* (methicillin sensitive and resistant variants); *Pseudomonas aeruginosa*; and *E. coli*. Common pathogenic forms of fungi and yeasts include *Trichophyton, Tinea* and *Candida albicans*. One of the major concerns of product manufacturers and end users of beauty products such as salons is the risk of microbial contamination and outbreaks of infections. In order to minimize this risk, the industry uses various strategies including preservatives, single use products and cleaning/sanitization procedures. The compositions of this invention are particularly useful in decreasing the risk of microbial contamination to the client in such spas or treatment facilities.

NUFREE® Finipil® (Equibal Labs, Unionville, N.Y.; U.S. Pat. No. 7,078,050 to Fusco) is a known mild bacteriostat and fungicide that is typically used after hair removal for slowing down hair regrowth and for soothing the skin.

Possibly relevant US patents and US patent application Publications that Applicant is aware of at the time of filing this application are the following:

US 2002/0034524 to Poret
US 2003/0049212 to Robinson et al.
US 2004/0022822 to Poret.
US 2004/0161435 to Gupta
US 2005/0025737 A1 to Sebagh
US 2005/0084471 to Andrews et al
US 2005/0053595 to Fusco
US2005/0249763 to Legendre et al.
US 2006/0115440 A1 to Arata et al.
US 2009/0186943 to Ikeda et al.
US 2009/0197948 to Mivahara et al.
US 2009/0203649 to Kato et al.
US 2009/0214628 to de Rijk
US 2009/0226498 to Flugge-Berendes et al.
US 2010/0196504 to Schmaus et al
US 2010/0216889 to Modak et al.
US 2011/0070316 to Modak et al.
US 2012/0148516 to Abel et al.
US 2012/0201902 to Modak et al.
US 2012/0276219 to Taylor et al.
US 2013/0005807 to Ishida et al
U.S. Pat. No. 5,879,684 to Fox
U.S. Pat. No. 5,997,893 to Jampani et al
U.S. Pat. No. 6,022,551 to Jampani et al
U.S. Pat. No. 6,022,565 to Albert et al
U.S. Pat. No. 6,528,070 to Bratescu et al
U.S. Pat. No. 7,078,050 to Fusco
U.S. Pat. No. 7,842,726 to Aoki et al.
U.S. Pat. No. 7,871,649 to Modak et al.
U.S. Pat. No. 8,173,143 to Tecco et al.
U.S. Pat. No. 8,198,326 to Scholz
U.S. Pat. No. 8,293,802 to Modak et al
U.S. Pat. No. 8,337,872 to Fuls et al.

Possibly relevant non-patent literature that Applicant is aware of at the time of filing this application are listed in the Information Disclosure Statement submitted with this application and copies are submitted therewith.

The entire disclosures of all of these aforementioned patents, publications and literature are incorporated herein by reference.

SUMMARY OF THE INVENTION

The invention is directed to topical, stable, self-preserving, antimicrobial, composition suitable for the treatment of a variety of dermal as well as subcutaneous conditions that includes an active ingredient a quaternary ammonium compound, preferably benzethonium chloride, potentiated and synergized with menthyl lactate in a cationic carrier. Optionally, a phenoxyethanol preservative and chlorhexidine digluconate antibacterial agent may be used to assist in enhancing the activity. The compositions kill a broad spectrum of gram-negative and gram-positive bacteria, fungus and yeasts. The compositions are used as first aid skin treatments and as skin sanitizers to help prevent bacterial contamination of minor cuts, scrapes and burns. The compositions are particularly useful when applied to the skin after hair removal in that they additionally cool, soothe and moisturize the skin. The compositions may also serve as a base vehicle in which additional skin care ingredients may be added to provide additional functionality to the compositions.

DETAILED DESCRIPTION OF THE DISCLOSED EMBODIMENT

Broadly, the present invention is directed to stable antibacterial and antimicrobial composition that includes a combination of an antimicrobial quaternary ammonium compound with menthyl lactate cooling agent in a cationic carrier containing at least one other skin care component.

Generally, the composition includes the following ingredients and ranges of ingredients:

| | |
|---|---|
| Water | 40.0-90.0% |
| Thickening agent: | 0.1-1.0% |
| Cationic synthetic or natural polymers | |
| Anti-microbial agent: | 0.01-0.2% |
| quaternary ammonium compounds | |
| Saturated fatty acids | 0.1-1.0% |
| Cationic conditioners | 0.1-10.0% |
| Cationic emulsifiers | 1.0-10.0% |
| Emollients | 0.1-10% |

-continued

| | |
|---|---|
| Fatty alcohols | 0.1-3.0% |
| Cooling agents | 1.0-10.0% |
| Herbal Extracts | 0.1-5.0% |
| Anti-irritants | 0.1-1.0% |
| Preservatives | 0.01-1.0% |

All ingredients are in weight/weight percent (w/w %), i.e., the weight of the ingredient relative to the weight of the final composition described as a percentage.

Water

The stable antibacterial and antimicrobial compositions of this invention contain from 40% to 90% water. In the preferred composition, the water is deionized water at a concentration of about 85%.

Thickening Agent: Cationic Synthetic or Natural Polymers

The composition of this invention additionally includes cationic thickening agents. The cationic thickening agents that may be used in this invention include Polyquaternium 10, 11, 16, 24, 37, and 67, chitosan and guar hydroxypropyltrimonium chloride, hydroxyethyl cetyldimonium phosphate, guar hydroxypropyltrimonium Chloride.

The preferred cationic thickening agent is Ultragel 300 (Cognis Corporation), also known as polyquaternium-37, and is a quaternium ammonium polymer consisting of primarily Ethanaminium, N,N,N-trimethyl-2-((2-methyl-1-oxo-2-propenyl)oxy)-, chloride, homopolymer. This composition is a cationic polymeric thickener typically used for producing transparent gel products in an acidic pH.

Preferred concentrations are from 0.1 to 1.0% by weight, with a highly concentration of 0.7% by weight.

Anti-Microbial Agent: Quaternary Ammonium Compounds

The preferred quaternary ammonium antimicrobial agent is benzethonium chloride. Benzethonium chloride is a monoalkyltrimethyl ammonium salt. This compound is an odorless white solid; soluble in water. It has surfactant, antiseptic, and anti-infective properties, and it is used as a topical antimicrobial agent in first aid antiseptics. It is also found in cosmetics and toiletries such as mouthwashes, anti-itch ointments, and antibacterial moist towelettes. Benzethonium chloride is also used in the food industry as a hard surface disinfectant.

Benzethonium chloride exhibits a broad spectrum of microbiocidal activity against bacteria, fungi, mold and viruses. Independent testing shows that benzethonium chloride is highly effective against such pathogens as methicillin-resistant *Staphylococcus aureus, Salmonella, Escherichia coli, Clostridium difficile*, hepatitis B virus, hepatitis C virus, herpes simplex virus (HSV), human immunodeficiency virus (HIV), respiratory syncytial virus (RSV), and norovirus.

The US Food and Drug Administration (FDA) specify that the safe and effective concentrations for benzethonium chloride are 0.1-0.2% in first aid and healthcare antiseptic drug products. Aqueous solutions of benzethonium chloride are not absorbed through the skin. It is not approved in the US and Europe for use as a food additive.

In addition to its highly effective antimicrobial activity, benzethonium chloride contains a positively charged nitrogen atom covalently bonded to four carbon atoms. This positive charge attracts it to the skin and hair. This contributes to a soft, powdery after feel on the skin and hair, as well as long-lasting persistent activity against microorganisms.

Benzethonium chloride is available under trade names Lonzagard, Salanine, BZT, Diapp, Quatrachlor, Polymine D, Phemithyn, Antiseptol, Disilyn, Phermerol, and others.

Other quaternary ammonium antimicrobial compounds that may be used alone or in combination with other similar compounds are methylbenzethonium chloride and benzalkonium chloride. If these antibacterial agents are used, the preferred concentrations are 0.01 to 0.13% by weight for benzalkonium chloride and 0.01 to 0.5% by weight methylbenzethonium chloride.

Other antibacterial agents that may be used, either alone or in combination are PCMX (para chloro neta xylenol), triclosan, ethanol, iodine and iodine complexes (e.g. PVI)

Saturated Fatty Acids

Saturated fatty acids selected from the group consisting of caprylic acid, capric acid, lauric acid, myristic acid, palmitic acid, stearic acid, arachidic acid, behenic acid, lignoceric acid, and cerotic acid. The preferred compositions of this invention include stearic acid, a saturated fatty acid with an 18 carbon chain and has the IUPAC name octadecanoic acid. The preferred concentration is from about 0.1 to 1.0% by weight, with a highly preferred concentration of 0.4% by weight.

Cationic Conditioners

Cationic conditioners and emulsifiers, which may be used according to the invention, include behentrimonium methosulfate, cetrimonium chloride, myristamidopropyl PG-dimonium chloride phosphate, brassicyl isoleucinate esylate.

The preferred composition of this invention includes behentrimmium methosulfate, with quantities of cetyl alcohol and butylene glycol, i.e., Incroquat™ Behenyl TMS-50 (Croda International, Plc). It assists in forming cationic skin care emulsions that impart wash resistant moisturizing benefits and a soft, smooth skin feel. Broadly, the concentration is from about 0.1 to 10.0% by weight, with a preferred concentration of 1.0% to 10% by weight, with a highly preferred composition at about 4% by weight.

Other cationic conditioners that can be used are Incroquat behenyl TMS, Incroquat behenyl TMS 50, cetrimonium chloride, distearyldimonium chloride, and stearalkonium chloride.

Emollients

Emollients selected from the group consisting of silicone fluids, emollient esters, emollient ethers, natural (avocado, coconut, safflower, etc.) and synthetic oils (mineral). The preferred compositions of this invention include dimethicones, preferably linear, polydimethylsiloxanes with viscosities ranging from 1.5 cSt to 20 million cSt. They are clear, colorless, odorless and inert fluids and are characterized by their softening effect on skin and hair. They are hydrophobic without restricting respiration of the skin that makes them beneficial in skin creams and lotions. Broadly, the concentration is from about 0.1 to 10.0% by weight, with a highly preferred composition at about 0.15% by weight.

Fatty Alcohols

Preferred fatty alcohols are selected from the group consisting of tert-Butyl alcohol, tert-Amyl alcohol, 3-Methyl-3-pentanol, ethchlorvynol, capryl alcohol, 2-ethyl hexanol, pelargonic alcohol, capric alcohol, undecyl alcohol, lauryl alcohol, tridecyl alcohol, myristyl alcohol, pentadecyl alcohol, cetyl alcohol, palmitoleyl alcohol, heptadecyl alcohol, stearyl alcohol, nonadecyl alcohol, arachidyl alcohol, heneicosyl alcohol, behenyl alcohol, erucyl alcohol, lignoceryl alcohol, ceryl alcohol, 1-heptacosanol, montanyl alcohol, cluytyl alcohol, myricyl alcohol, melissyl alcohol, geddyl alcohol, and cetearyl alcohol, oleyl Alcohol and octyldodecanol.

The preferred compositions of this invention include 2-octyldodecanol, Eutanol® G (Cognis). This is a "medium spreading" emollient that is hydrolysis stable and typically used in formulations where a wide pH range is needed e.g.

deodorants, antiperspirants, cosmetic and pharmaceutical skin care preparations and for hair remover formulations.

The preferred compositions of this invention also include cetyl alcohol, also known as 1-hexadecanol and palmityl alcohol, is a fatty alcohol with the formula CH3(CH2)15OH.

Broadly, the concentration of fatty alcohol is from about 0.1 to 3.0% by weight, with a preferred composition containing 0.1 to 3.0% by weight 2-octyldodecanol and 0.1% to 2.0% phenoxyethanol, with the highly preferred composition containing 3.0% by weight 2-octyldodecanol and 0.5% phenoxyethanol.

Cooling Agents

The compositions of this invention further include a cooling agent, which provides, when applied to the skin, a cooling or soothing feeling. The highly preferred cooling agent used in this invention is menthyl lactate. Other cooling agents, which may be used according to the invention, include, but are not limited to natural and synthetic menthol derivatives. Menthyl lactate (Frescolate®) has a mild, cooling, fresh, minty, somewhat burnt sugar like and sweet menthol taste profile. It is used in minty compounds for various purposes such as toothpaste, chewing gum and tobacco. It is also used in confections, beverages, and as a peppermint booster in oral care products. Menthyl lactate is produced in two forms, a white crystalline powder and fused material; both forms are used in various applications. It has been discovered that in a cationic carrier the antimicrobial agent is potentiated and synergized with menthyl lactate cooling agent. Broadly, the concentration is from about 1.0 to 10.0% by weight, with a highly preferred composition at about 4.5% by weight.

Herbal Extracts and Anti-Irritants

Herbal extracts and anti-irritants selected from the group consisting of chamomile, bisabolol, aloe vera, panthenol, zinc salts, calendula, oat extracts, azulene, camellia oil, witch-hazel extract. The preferred compositions of this invention also include chamomile or chamomile. This is a common name for several daisy-like plants of the family Asteraceae.

It is preferred to add chamomile to skin cosmetics to serve as an emollient and its anti-inflammatory effects. Broadly, the concentration is from about 0.1 to 5.0% by weight, with a highly preferred composition at about 0.3% by weight.

The preferred compositions of this invention also contain witch hazel as an astringent. Broadly, the concentration is from about 0.1 to 5.0% by weight, with a highly preferred composition at about 0.3% by weight.

The preferred composition of this invention also include bisabolol, or more formally α-(-) bisabolol or levomenol. This is a natural monocyclic sesquiterpene alcohol. It is colorless, viscous oil that is the primary constituent of the essential oil from German chamomile (*Matricaria recutita*) and *Myoporum crassifolium*. It is almost insoluble in water and glycerin, but soluble in ethanol. Bisabolol has a weak sweet floral aroma and is used in various fragrances. Bisabolol is known to have anti-irritant, anti-inflammatory and anti-microbial properties. Bisabolol is also demonstrated to enhance the percutaneous absorption of certain molecules. Broadly, the concentration is from about 0.1 to 1.0% by weight, with a highly preferred composition at about 0.3% by weight.

Humectants selected from the groups consisting of glycerin, propylene glycol, polyethylene glycol, glycereth-26, acetamide MEA, sorbitol may also be added to the composition.

Preservatives

The topical compositions of this invention also contain a preservative or preservative system to inhibit the growth of pathogens over an extended period. The preferred preservative system consists of one or more of the following ingredients, chlorhexidine and its salts, polyhexamethylene biguanide, alexidine, triclosan, parachlorometaxylenol, zinc pyrithione, silver and silver salts, parabens, Methylisothiazolinone, organic acids (citric, acetic, sorbic, lactate), phenoxyethanol, phenethyethanol, essential oils (tea tree, eucaplyptus, thyme). The preferred preservative is Neolone 100, which is phenoxyethanaol available from Dow. Other suitable preservatives for use may be used, although Neolone 100 is the preferred.

The preferred compositions of this invention also include chlorhexidine digluconate, i.e., CHG (20%). This is a 20% aqueous solution of 1,6-BIS (N—P-Chlorophenyl-Biguanido) and Hexane Digluconate and has powerful activity against bacteria and fungi at low concentrations. It is effective against gram-negative and gram-positive bacteria. Its effectiveness is enhanced in alcohols and its activity is unaffected by the presence of blood and other biological fluids. Broadly, the concentration of preservative is from about 0.01 to 1.0% by weight, with a highly preferred composition at about 0.25% by weight.

Other preservatives that can be used alone or in combination herein are Chlorhexidine gluconate, chlorhexidine acetate, chlorhexidine chloride, and chlorhexidine, free-base, Phenoxyethanol, parabens, such as methyl paraben, ethyl parabens, propyl parabens, butyl paraben and synergistic paraben blends, Kathon, acidifiers, such as citric, acetic, latic, malic acids, silver and silver salts, copper and copper salts, zinc and zinc salts, DMDM Hydantoin, Imidazolidinyl Urea, Iodopropynyl Butyl Carbamate, Benzoic Acid, Sodium benzoate, Potassium benzoate, PHMB, Zinc pyrithione.

Additional Ingredients

The topical, stable, self-preserving, antimicrobial, compositions of this invention may further include other ingredients to provide a desired functionality, for example:

Sunscreens aminobenzoic acid, arobenzone, cinoxate, diioxybenzone, homosalate, menthyl anthranilate, octocrylene, octyl methoxycinnamate, octyl salicylate, oxybenzoate, padimate 0, phenylbenzimidazole, sulfonic acid, sulisobenzone, titanium dioxide, trolamine salicylate and zinc oxide.

Antimicrobials

The compositions of the invention may further include one or more additional antimicrobial agents, for example antiviral, antibacterial, or antifungal substances. Antimicrobial agents also include substances possessing any combination of virucidal or virustatic, bacteriocidal or bacteriostatic, or fungicidal or fungistatic properties.

Examples of antimicrobial agents include, but are not limited to, iodophors, iodine, benzoic acid, dehydro acetic acid, propionic acid, sorbic acid, methyl paraben, ethyl paraben, propyl paraben, butyl paraben, cetrimide, chlorhexidine (free base and/or salts), other biguanides, such as polyhexamethylene biguanide (PHMB) and polyaminopropyl biguanide (PAPB), chloroeresol, chloroxylenol, benzyl alcohol, bronopol, chlorbutanol, ethanol, isopropyl alcohol, n-propanol, phenoxyethanol, phenylethyl alcohol, 2,4-dichlorobenzyl alcohol, thiomersal, clindamycin, erythromycin, benzoyl peroxide, mupirocin, bacitracin, polymyxin B, neomycin, triclosan, parachlorometaxylenol, foscarnet, miconazole, fluconazole, itriconazole, ketoconazole, and pharmaceutically acceptable salts thereof.

Antibiotics

The compositions of the invention may further include one or more antibiotics such as penicillin (natural, semi-synthetic and synthetic), minocycline, rifampin, fluoroquinolones (ciprofloxacin), nalidixic acid, sulfa drugs (sulfadiazine, sulfamethoxazole, sulfacetamide, sulfadoxine), silver (metallic and nano) and silver salts (silver sulfadiazine, silver nitrate, silver oxide, silver carbonate, silver chloride), copper and copper salts, zinc and zinc salts, ethyl alcohol, mupirocin, and benzoyl peroxide.

Wax Emulsifiers

The compositions of the invention may further include one or more solid waxy esters, for example, Myristyl Myristate, Cetyl Palmitate, Myristyl Stearate, Stearyl Behenate, Behenyl Isostearate, Isostearyl Behenate, Behenyl Behenate, Lauryl Behenate, Behenyl Erucate, Polawax, for example, cationic: Incroquat TMS, Incroquat TMS50 (Croda International, Plc)

The following is a list of ingredients in the preferred compositions of this invention and the ranges of such ingredients that may be used.

| INGREDIENT | Generic name | % (w/w) Preferred | Range (about % w/w) |
|---|---|---|---|
| Deionized water | Water | 84.8 | 40.0-90.0 |
| Ultragel 300 or *Polyquarternium-37 | Quaternary ammonium polymer | 0.7 | 0.1-1.0 |
| Benzethonium Chloride | | 0.2 | .01-0.2 |
| Emersol 132 (Stearic acid) | Stearic Acid | 0.4 | 0.1-1.0 |
| Eutanol G | 2-octyldodecanol | 3.0 | 0.1-3.0 |
| Incroquat Behenyl TMS-50 | Behentrimonium methosulfate (and) Cetyl alcohol (and) Butylene glycol | 4.0 | 1.0-10.0 |
| Dimethicone DC200 | Linear Polydimethylsiloxane Fluids | 0.15 | 0.1-10 |
| Cetyl alcohol | 1-hexadecanol or palmityl alcohol | 0.6 | .5-3.0 |
| Frescolate | Menthyl Lactate | 4.5 | 1.0 10.0 |
| Neolone PH 100 | Phenoxyethanol | 0.5 | 0.1-2.0 |
| Chamomile extract Chamomile Recutita | Matricaria Extract | 0.3 | 0.1-5.0 |
| Witch hazel extract | Hamamelis Virginiana | 0.3 | 0.1-5.0 |
| Bisabolol | α-(-)-bisabolol or also known as levomenol | 0.3 | 0.1-1.0 |
| CHG (20%) | 20% Chlorhexidine Gluconate Solution | 0.25 | .001-.5 |

*Polyquaternium-37, i.e., Poly(2-methacryloxyethyltrimethylammonium chloride)

The highly preferred stable, antimicrobial topical treatment composition consists essentially of the following ingredients and concentrations (weight percent):

| | |
|---|---|
| Water | 84.8% |
| Quaternary ammonium polymer | 0.7% |
| Benzethonium Chloride | 0.2% |
| Stearic Acid | 0.4% |
| 2-octyldodecanol | 3.0% |
| Behentrimonium methosulfate | 4.0% |
| Linear Polydimethylsiloxane fluids | 0.15% |
| Cetyl alcohol | .6% |
| Menthyl Lactate | 4.5% |
| Phenoxyethanol | 0.5% |
| Chamomile Extract | 0.3% |
| Witch hazel extract | 0.3% |
| Bisabalol | 0.3% |
| 20% Chlorhexidine Gluconate Solution | .25% |

The combination of ingredients in the composition of this invention, when properly combined, form a unique antibacterial and antimicrobial composition. The composition can be used as a first aid skin treatment to help prevent bacterial contamination of minor cuts, scrapes and burns. The composition cools, soothes and moisturizes the skin after hair removal. The composition kills bacteria, fungus and yeast, including *Staphylococcus aureus, Pseudomonas aeruginosa, Escherichia coli, Aspergillus brasiliensis*, and *Candida albicans*.

The composition, although useful as a topical application after hair removal, may also be used as an anti-inflammatory for poison ivy, acne and other type skin disorders, a sanitizer and as an antiseptic first aid composition.

The compositions, although preferably liquid, made be made into a spray, cream gel and lotion for different applications.

The ingredients for the compositions of this invention, particularly the preferred compositions, are chemically compatible with each other. Broadly, the process of the producing the compositions, includes the following:

Step A. Combine the selected amounts of water, cationic synthetic or natural polymers until fully blended at 16° C.-25° C. Continue blending and heat to a range of 55° C. to 75° C. and hold for a period of time.

Step B. Heat to 40° C. to 75° C. and blend the selected amounts of Cationic conditioners, Cationic emulsifiers, Fatty alcohols, Saturated Fatty Acids, Cooling agents and emollients and hold for a period of time.

Step C. Add the selected amount Antimicrobial Quaternary Ammonium compounds and blend with the mixture of Step A at 60° C. to 70° C.

Step D. Combine and Blend mixture of Step C with that of Step A and begin cooling the blend to 22° C. to 35° C.

Step E. During the cooling step of Step D when the temperature reaches 40° C. to 35° C. blend in the Herbal Extracts, Anti Irritants, Preservatives. Continue Blending until the desired Viscosity is achieved.

The following are some specific, non-limiting examples of the compositions of this invention. The compositions may further include additional ingredients, which do not substantially affect the antimicrobial activities of the composition.

Example 1

| First aid antiseptic and soothing lotion comprising | |
|---|---|
| Deionized water (USP) | 81.4% w/w |
| DC200 Dimethicone | 1.0% w/w |
| Dehyquart C4046 | 4.0% w/w |
| Benzethonium chloride | 0.2% w/w |
| Cyclomethicone | 5.0% w/w |

| First aid antiseptic and soothing lotion comprising | |
|---|---|
| Frescolat ML | 4.5% w/w |
| Chlorhexidine gluconate (20%) | 0.2% w/w |
| Eutanol G | 3.0% w/w |
| Phenoxyethanol | 0.7% w/w |

Observations:

The composition remains stable after three freeze/thaw cycles, i.e., the ingredients are compatible and the composition is stable.

Example 2

| First aid antiseptic lotion | |
|---|---|
| Deionized water (USP) | 83.0% w/w |
| DC200 Dimethicone | 1.0% w/w |
| Incroquat behenyl TMS 50 | 4.0% w/w |
| Benzethonium chloride | 0.2% w/w |
| Witch hazel extract | 0.3% w/w |
| Frescolat ML | 4.5% w/w |
| Chlorhexidine gluconate (20%) | 1.0% w/w |
| Eutanol G | 3.0% w/w |
| Phenoxyethanol | 0.7% w/w |
| Cyclomethicone | 5.0% w/w |
| Bisabolol | 0.3% w/w |

Observations:

The formulation is very liquid and does not survive the freeze/thaw test due to separation. This indicates some incompatibility between one or more ingredients.

Example 3

| First aid antiseptic and cooling cream | |
|---|---|
| Deionized water (USP) | 78.7% w/w |
| DC200 Dimethicone | 1.0% w/w |
| Crodafos CES | 6.0% w/w |
| Benzethonium chloride | 0.2% w/w |
| Witch hazel extract | 0.3% w/w |
| Frescolat ML | 4.5% w/w |
| Chlorhexidine gluconate (20%) | 1.0% w/w |
| Zemea | 3.0% w/w |
| Phenoxyethanol | 0.7% w/w |
| Cyclomethicone | 5.0% w/w |
| Bisabolol | 0.3% w/w |

Observations:

The formulation is stable after 3 freeze/thaw cycles

Example 4

| First aid antiseptic and skin sanitizing cooling cream | |
|---|---|
| Deionized water (USP) | 84.6% w/w |
| DC200 Dimethicone | 1.0% w/w |
| Eutanol G | 3.0% w/w |
| Chamomile extract | 0.3% w/w |
| Benzethonium chloride | 0.2% w/w |
| Witch hazel extract | 0.3% w/w |
| Frescolat ML | 4.5% w/w |
| Chlorhexidine gluconate (20%) | 1.0% w/w |
| Stearic acid | 0.4% w/w |
| Cetyl alcohol | 0.6% w/w |
| Ultragel 300 | 0.7% w/w |
| Phenoxyethanol | 0.7% w/w |
| Incroquat TMS50 | 4.0% w/w |
| Bisabolol | 0.3% w/w |

Observations:

The formulation is stable after 3 freeze/thaw cycles.

Antimicrobial Activity

This example determines the antimicrobial activity of the preferred composition of this invention (hereinafter "OTC") as an OTC antiseptic cream using a modified time kill method based on ASTM E2315-03 and a zone of inhibition assay.

1. Equibal Labs Finipil® Batch #04092612 (the composition of U.S. Pat. No. 7,078,050 to Fusco, "Finipil")
2. The preferred composition of this invention with 0.2% Benzethonium chloride; Batch #01021913 ("OTC")—Example 4, above.
    a. Note: All the following OTC compositions are Example 4 herein.

The following tests are used to determine the efficacy of the OTC formulation compared to the original Finipil formulation and a competitive product:

Example A

Modified ASTM Method E2315-03 In Vitro 10 Minute Time Kill Assays

An aliquot of 0.8 ml of test product (Finipil® is tested against *S. aureus*) is pre-warmed to 35° C. is mixed with 0.2 ml of a mixture of 50% culture (approx 22 hours old), diluted to 0.45 OD at 600 nm with the appropriate medium and sterile bovine adult serum (so that the BAS comprises 50% of the inoculum's volume) and mixed well. The tubes are then incubated at 35° C. for 10 minutes. After the time has elapsed, 0.2 ml of the contents of the tube is transferred to a tube containing 4.8 ml of D/E broth to quench the antimicrobial activity. After thoroughly mixing the contents to ensure that the product is evenly suspended, 0.5 ml of is plated on TSA (SDA plates for yeast and fungus) plates are incubated for 24-48 hours at 35° C. to 37° C. (up to five days at 21° C. for fungus).

As a control, 0.8 ml of sterile normal saline is substituted for the test product. 0.5 ml of the control sample is plated after processing as follows: the control is diluted according to the same initial dilution scheme as the test samples followed by a dilution in TSB of 1:1000 for a final dilution of 1:50,000 (0.01 ml of the 1:50 dilution tube: 9.99 ml TSB) and 0.5 ml of this final dilution are plated on TSA. In the case of yeast, the control samples are diluted 1:100 with SDB for a final dilution of 1:5000 plated on SDA. The fungus control is diluted and plated in the same manner as the test samples using SDA.

A saline+D/E broth uninoculated blank is also subcultured to ensure sterility of the media and technique.

Test Organisms:
a. *Staphylococcus aureus* ATCC #6538
b. *Pseudomonas aeruginosa* ATCC #9027
c. *Escherichia coli* ATCC #8739
d. *Staphylococcus aureus* ATCC #33592 (Methicillin Resistant)
e. *Aspergillus brasiliensis* ATCC #16404
f. *Candida albicans* ATCC #10231

Test Groups:

3. Equibal Labs Finipil®; Batch #04092612 (the composition of U.S. Pat. No. 7,078,050 to Fusco, "Finipil")
4. "OTC" as described in Formula 4 above
5. Competitive cream-commercially available post depilatory cream Results:

TABLE 1

Results expressed as % reduction of microbes in the test group versus the control group after a 10 minute exposure.

| Challenge Organism | Control cfu/ml | OTC cfu/ml | OTC % reduction | Competitive Product cfu/ml | Competitive Product % reduction |
|---|---|---|---|---|---|
| S. aureus ATCC 6538 | $4.4 \times 10^7$ | <49 | >99.9998 | $3.4 \times 10^7$ | 22.73 |
| S. aureus ATCC 33592 | $3.1 \times 10^7$ | <49 | >99.9998 | $2.3 \times 10^7$ | 27.42 |
| P. aeruginosa ATCC 9027 | $2.9 \times 10^8$ | <49 | >99.9999 | $1.6 \times 10^8$ | 44.83 |
| E. coli ATCC 8739 | $1.9 \times 10^8$ | <49 | >99.9999 | $1.4 \times 10^8$ | 29 |
| C. albicans ATCC 10231 | $1.2 \times 10^6$ | <49 | >99.996 | $1.1 \times 10^6$ | 8.33 |
| A. brasiliensis ATCC 16404 | $2.5 \times 10^3$ | <49 | >98 | $1.6 \times 10^3$ | 38 |

| Challenge Organism | Control cfu/ml | OTC (0.2% BZT) cfu/ml | OTC (0.2% BZT) % reduction | Finipil cfu/ml | Finipil % reduction |
|---|---|---|---|---|---|
| S. aureus ATCC 6538 | $3.7 \times 10^7$ | <49 | >99.9999 | $2.4 \times 10^7$ | 36.49 |

The OTC formulation is highly efficacious compared to either the competitive product or the Finipil. Only the OTC group meets the FDA requirements of a 3 log reduction of pathogens in 10 minutes.

Example B

Zone of Inhibition Test Comparing OTC and One Competitive Product

An overnight culture of the test organism is diluted to 0.40 OD at 600 nm and then further diluted $10^{-2}$ to obtain approximately $3 \times 10^6$ CFU/ml for the inoculation of TSA or SDA plates as follows: a 0.5 ml volume is spread across the surface of a sterile agar plate and allowed to dry. A 7 mm well is made in the center of the agar plate and approximately 0.2 ml of product is pipetted into the well. Additionally, Finipil is tested against S. aureus. The plates are incubated at 37° C. for 24 hours and the zones of inhibition are determined by measuring the diameter of the clear circular area around the product filled well.

The following organisms will be used for this test:
Staphylococcus aureus ATCC 6538 (MSSA)*
Staphylococcus aureus ATCC 33592 (MRSA)*
Pseudomonas aeruginosa ATCC 9027
Escherichia coli ATCC 8739
Candida albicans ATCC 10231
Aspergillus brasiliensis ATCC #16404
*Becton Dickinson BBL Cefoxitin 30 microgram Sensi-Disk® sensitivity disks will be used to indicate susceptibility to Methicillin Results:

TABLE 2

Zone of inhibition test comparing OTC, Finipil and one competitive product.

| Challenge Organism | Cefoxitin disk Zone (mm) | OTC Zone (mm) | Competitive Product Zone (mm) | Finipil Zone (mm) |
|---|---|---|---|---|
| S. aureus ATCC 6538 | 33 | 24 | 11 | 12 |
| S. aureus ATCC 33592* | 10 | 24 | 13 | ND |
| P. aeruginosa ATCC 9027 | ND | 15 | 10 | ND |
| E. coli ATCC 8739 | ND | 17 | 8 | ND |
| C. albicans ATCC 10231 | ND | 13 | 0 | ND |
| A. brasiliensis ATCC 16404 | ND | 15 | 14 | ND |

ND = Not done;
*Characterized as Methicillin resistant by ATCC

OTC shows broad-spectrum activity against all of the pathogens tested. The competitive product and the Finipil® showed low level inhibition of growth. The competitive product does not appear to possess any activity, even over a 24 hour time period against C. albicans ATCC 10231.

The activity of OTC does not appear to be affected by the resistance profile of the S. aureus variant used as the challenge organism. As the data in the above table shows, S. aureus ATCC 33592 shows significant resistance to Cefoxitin, a Methicillin analog, compared to a known Methicillin-sensitive isolate, S. aureus ATCC 6538, where the Cefoxitin sensitivity disk produced a large zone of inhibition.

Example C

Modified ASTM Method E2315-03 In Vitro 15 Second Time Kill Assays Comparing a) Finipil with 0.2% w/w Benzethonium Chloride Added, b) Finipil, and c) OTC The purpose of this test is to compare the antibacterial efficacy of a) Finipil with 0.2% w/w benzethonium chloride added, b) Finipil, and c) OTC.

A 0.9 ml volume of test product is mixed with 0.1 ml of an overnight culture (approx 22 hours old) of S. aureus ATCC 6538, diluted to 0.45 OD at 600 nm, and mixed for 15 seconds. After the time has elapsed, 0.2 ml of the culture/product is removed and added to 4.8 ml of D/E broth quench antimicrobial the activity and a 0.5 ml aliquot is plated on TSA. The TSA plates are incubated for 24-48 hours at 35° C. to 37° C. As a control, 0.9 ml of sterile normal saline is substituted for the test products. 0.5 ml of the control is plated after a 1:1000 dilution of the D/E broth tube (0.01 ml: 9.99 ml). A saline+ D/E broth uninoculated blank is also subcultured to ensure sterility of the media and technique.

Results:

TABLE 3

Comparative kill rate of OTC and Finipil with and without benzethonium chloride (BZT)

| Challenge Organism | % Reduction in 15 seconds | | |
|---|---|---|---|
| | OTC | Finipil | Finipil + BZT |
| S. aureus ATCC 6538 | 99.95 | 20 | 32 |

OTC exhibits superior antibacterial activity against S. aureus ATCC 6538 compared to the original Finipil formula or the original Finipil formula with the mere addition of 0.2% BZT. The addition of benzethonium chloride to the Finipil formula does not seem to provide any significant boost to the antibacterial effect. Without being bound to any particular theory, this may be due to the binding or complexing of the cationic BZT with anionic or non-ionic ingredients. The cationic nature of the OTC appears to enhance the activity of the BZT and may also support the synergistic antibacterial effect of one or more of the ingredients. It is also notable that the menthyl lactate does not appear to have any significant antibacterial efficacy (20% reduction) in a non-cationic based formulation such as Finipil.

Example D

Modified ASTM Method E2315-03 In Vitro 15 Second Time Kill Assays for the Determination of the Efficacy of OTC as a Health Care Antiseptic Drug Product The same test protocol is used as described in Example C above.

Results:

| Challenge Organism | % Reduction in 15 seconds |
|---|---|
| | OTC |
| P. aeruginosa ATCC 9027 | >99.99996 |
| S. aureus ATCC 6538 | 99.99 |
| S. aureus ATCC 33592* | 99.9 |
| E. coli ATCC 8739 | 99.99999 |
| C. albicans ATCC 10231 | 99.998 |

OTC meets the efficacy requirements of the FDA TFM for healthcare antiseptic drug products against the pathogens tested.

Example E

Determination of the combined and separate antibacterial effects of benzethonium chloride and menthyl lactate in the cationic base used in the OTC formulation.

Briefly, OTC and derivative formulations are made as follows:

1) OTC with 4.5% w/w menthyl lactate without benzethonium chloride
2) OTC with 0.2% benzethonium chloride without menthyl lactate
3) OTC with both 0.2% benzethonium chloride and 4.5% menthyl lactate The formulations are tested using the same test protocol is used as described in Example C above.

Results:

| Challenge Organism | 15 second $\log_{10}$ reduction in CFU from control | | |
|---|---|---|---|
| | OTC | OTC without BZT | OTC without menthyl lactate |
| S. aureus ATCC 6538 | 4.0 | 1.2 | 2.6 |

The results indicate the following: 1) that there is a slight synergy between the BZT and menthyl lactate, and 2) the antimicrobial activity of menthyl lactate is greater in a cationic base compared to an anionic base. Without being bound to any particular theory, this same phenomenon may hold true for other natural, semi-synthetic, and fully synthetic menthol derivatives.

In summary, the compositions of this invention may be used as a first aid skin treatment to help prevent bacterial contamination of minor cuts, scrapes and burns. Unexpectedly the antimicrobial efficacy is vastly greater in a cationic system. There appears to be a potentiation or synergism between the quaternary ammonium compounds and the menthyl lactate in a cationic system.

It is preferred to use the compositions immediately after the removal of hair from the skin, weather by shaving, waxing, depilatory cream shaves or the use of wax free, non-aqueous (anhydrous) liquid depilatories, e.g., NUFREE® brand depilatories (Equibal Labs, Unionville, N.Y.). See also U.S. Ser. No. 13/712,937 filed on Dec. 12, 2012 entitled Antibacterial Hair Removal Composition to Normajean Fusco. The entire disclosure of this application is incorporated herein by reference. The compositions cool, soothe and moisturize the skin after hair removal.

More specifically, the compositions of this invention are 100% effective as an antibacterial, antimicrobial treatment. The compositions kill bacteria, fungus and yeast, including Staphylococcus aureus, MRSA, Pseudomonas aeruginosa, Escherichia coli, Aspergillus brasiliensis, and Candida albicans.

When applied to the skin after shaving or hair removal it cools, shrinks, reduces swelling and protects the empty hair follicles, increases elasticity in the hair follicle wall, breaks fats and oils to prevent clogging of the hair follicle, atrophies new hair growth, and when used daily, drops the temperature of the empty follicle, freezing away swelling due to water retention, hot showers or aerobic workouts and protects against in-grown hairs and rids the area of old in-growns.

The compositions of this invention may also be used when you need an antibacterial and antimicrobial skin treatment along with instant cooling and soothing. It may also be used during a manicure or pedicure to heal and soothe cuticle damage, and kills fungus or used on feet at the health club to reduce swelling and prevent the growth of bacteria. The composition may also be used to sooth chapped lips and cold sores. Due to the rapid kill capabilities demonstrated by the compositions of this invention, they may be used as a healthcare antiseptics and hand sanitizers.

What is claimed:

1. A method of treating bacterial contamination in the skin of a human in need thereof consisting essentially of administering to the skin of the human a stable, antimicrobial composition consisting essentially of:
   i. a cationic thickener selected from the group consisting of Polyquaternium, chitosan, hydroxyethyl cetyldimonium phosphate, and guar hydroxypropyltrimonium Chloride; and ii. a cationic conditioning agent and emulsifier which are selected from the group consisting of behentrimonium methosulfate, cetrimonium chloride, myristamidopropyl PG-dimonium chloride phosphate, brassicyl isoleucinate esylate, Incroquat behenyl TMS, Incroquat behenyl TMS 50, cetrimonium chloride, distearyldimonium chloride, and stearalkonium chloride; and iii. an effective antimicrobial amount of a component selected from the group consisting of polyhexamethylene biguanide, polyaminopropyl biguanide, alexidine, benzalkonium chloride, benzethonium chloride, methylbenzethonium chloride, cetrimonium chloride, and lysine; and iv. an amount of a menthol-based cooling agent.

2. The method of claim 1, wherein the amount of the menthol based cooling agent in the antimicrobial composition is between 0.1 to 7.0% by weight.

3. The method of claim 1, wherein the effective antimicrobial amount of the antimicrobial agent is between 0.01% to 5% by weight.

4. The method of claim 1, wherein the antimicrobial agent is selected from the group consisting of:
   b. Benzethonium chloride wherein the effective antimicrobial amount is from 0.01 to 0.2% w/w;
   c. Benzalkonium chloride wherein the effective antimicrobial amount is from 0.01 to 0.13% w/w; and
   d. Methylbenzethonium chloride wherein the effective antimicrobial amount is 0.01 to 0.5% w/w.

5. A method of treating bacterial contamination in the skin of a human in need thereof consisting essentially of administering to the skin of the human a therapeutically effective amount of a stable, antimicrobial composition consisting essentially of:
   i. a cationic thickener selected from the group consisting of Polyquaternium, chitosan, hydroxyethyl cetyldimonium phosphate, and guar hydroxypropyltrimonium Chloride; and
   ii. a cationic conditioning agent and emulsifier which are selected from the group consisting of behentrimonium methosulfate, cetrimonium chloride, myristamidopropyl PG-dimonium chloride phosphate, brassicyl isoleucinate esylate, Incroquat behenyl TMS, Incroquat behenyl TMS 50, cetrimonium chloride, distearyldimonium chloride, and stearalkonium chloride; and
   iii. an effective antimicrobial amount of a component selected from the group consisting of polyhexamethylene biguanide, polyaminopropyl biguanide, alexidine, benzalkonium chloride, benzethonium chloride, methylbenzethonium chloride, cetrimonium chloride, and lysine;
   iv. an amount of a menthol-based cooling agent and;
   v. a non-ionic thickener.

6. A method of treating bacterial contamination in the skin of a human in need thereof consisting essentially of administering to the skin of the human a therapeutically effective amount of a stable antimicrobial composition consisting essentially of:
   i. a cationic thickener selected from the group consisting of Polyquaternium, chitosan, hydroxyethyl cetyldimonium phosphate, and guar hydroxypropyltrimonium Chloride; and
   ii. a cationic conditioning agent and emulsifier which are selected from the group consisting of behentrimonium methosulfate, cetrimonium chloride, myristamidopropyl PG-dimonium chloride phosphate, brassicyl isoleucinate esylate, Incroquat behenyl TMS, Incroquat behenyl TMS 50, cetrimonium chloride, distearyldimonium chloride, and stearalkonium chloride; and
   iii. an effective antimicrobial amount of a component selected from the group consisting of polyhexamethylene biguanide, polyaminopropyl biguanide, alexidine, benzalkonium chloride, benzethonium chloride, methylbenzethonium chloride, cetrimonium chloride, and lysine; and
   iv. an amount of a menthol-based cooling agent and;
   v. an amount of a non-ionic conditioning agent and a non-ionic emulsifying agent.

* * * * *